United States Patent
Jain et al.

(10) Patent No.: US 10,836,765 B2
(45) Date of Patent: Nov. 17, 2020

(54) PROCESS FOR THE PREPARATION OF VALACYCLOVIR

(71) Applicants: AUROBINDO PHARMA LTD, Hyderabad (IN); Sandeep Jain, Hyderabad (IN); Komel Ansari, Hyderabad (IN); Subramanyam Maddala, Hyderabad (IN); Sivakumaran Meenakshisundaram, Hyderabad (IN)

(72) Inventors: Sandeep Jain, Hyderabad (IN); Komel Ansari, Hyderabad (IN); Subramanyam Maddala, Hyderabad (IN); Sivakumaran Meenakshisundaram, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 18 days.

(21) Appl. No.: 16/081,944

(22) PCT Filed: Feb. 24, 2017

(86) PCT No.: PCT/IB2017/051066
§ 371 (c)(1),
(2) Date: Sep. 3, 2018

(87) PCT Pub. No.: WO2017/149420
PCT Pub. Date: Sep. 8, 2017

(65) Prior Publication Data
US 2019/0023706 A1 Jan. 24, 2019

(30) Foreign Application Priority Data

Mar. 3, 2016 (IN) .............................. 201641007467

(51) Int. Cl.
*C07D 473/18* (2006.01)
*B01J 19/00* (2006.01)

(52) U.S. Cl.
CPC ......... *C07D 473/18* (2013.01); *B01J 19/0093* (2013.01); *B01J 2219/00033* (2013.01)

(58) Field of Classification Search
CPC .................................................... C07D 473/18
See application file for complete search history.

(56) References Cited

U.S. PATENT DOCUMENTS 6,849,737 B2 * 2/2005 Etinger ................ C07D 473/00
544/276

OTHER PUBLICATIONS

Wiles, Charlotte. Eur. J. Org. Chem. (2008) 1655-1671.*
Wiles, Charlotte. Green Chem., 2012 14, 38. (Year: 2012).*

* cited by examiner

*Primary Examiner* — Emily A Bernhardt
*Assistant Examiner* — Laura M Daniel
(74) *Attorney, Agent, or Firm* — Jay R Akhave

(57) ABSTRACT

The present invention relates to an improved process for the preparation of Valacyclovir or pharmaceutically acceptable salts thereof, which comprises reaction of amine-protected Valacyclovir or its salt with deprotecting agent in a continuous flow reactor.

2 Claims, No Drawings

PROCESS FOR THE PREPARATION OF VALACYCLOVIR

FIELD OF THE INVENTION

The present invention relates to an improved process for the preparation of Valacyclovir or pharmaceutically acceptable salts thereof.

BACKGROUND OF THE INVENTION

Valacyclovir, chemically known as 2-[(2-amino-1,6-dihydro-6-oxo-9H-purin-9-yl)methoxy]ethyl L-valinate and has a structure of formula I:

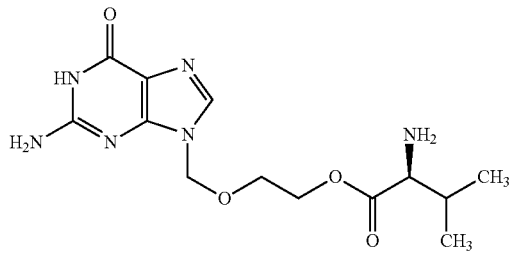

I

Valacyclovir, which is marketed in the form of its hydrochloride salt is an antiviral drug approved in United States and several other countries under the trade name VALTREX®. Valacyclovir hydrochloride is used in the treatment of viral infections such as Herpes Zoster and Genital Herpes in humans.

Valacyclovir is a prodrug that is derived from acyclovir by esterification of 3'-hydroxyl group of Acyclovir with L-valine. Acyclovir is also an antiviral nucleoside that possesses activity against human herpes viruses. Valacyclovir has enhanced bioavailability, when compared to Acyclovir.

Valacyclovir and its pharmaceutically acceptable salts were disclosed in the U.S. Pat. No. 4,957,924. The U.S. Pat. No. '924 discloses processes for the preparation of Valacyclovir, which involves esterification of Acyclovir with Carboxybenzyl (Cbz) protected Valine in presence of N,N'-dicyclohexylcarbodiimide (DCC) and 4-(Dimethylamino)pyridine (DMAP) in dimethylformamide to obtain Cbz-protected Valacyclovir, which is subsequently deprotected to obtain Valacyclovir. The process is as summarized in scheme 1.

Scheme-1:

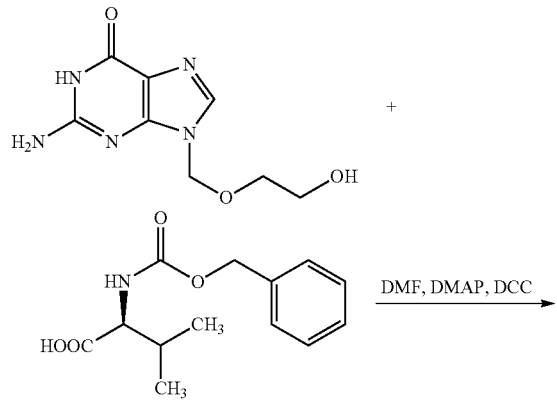

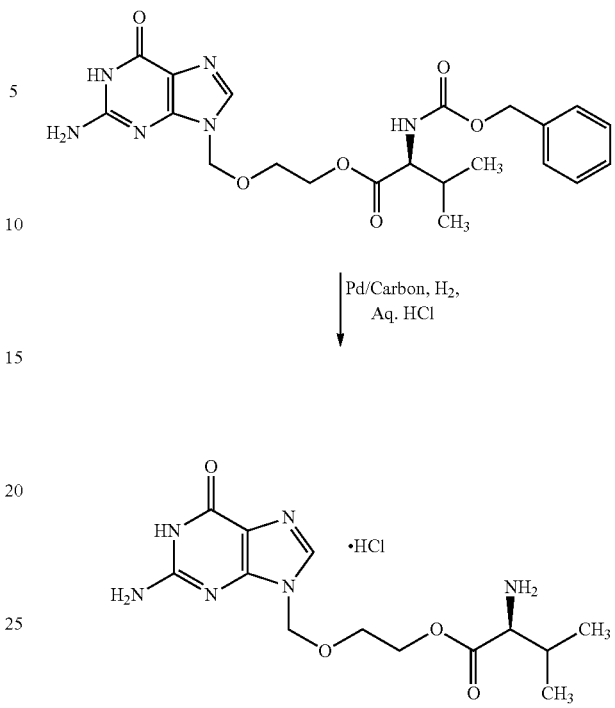

This process requires the removal Cbz group by catalytic hydrogenation using hydrogen gas and specialized equipment such as an autoclave.

U.S. Pat. No. 6,849,737 discloses alternate process for the preparation of Valacyclovir using less severe deprotecting procedures and different protection group viz. tert-butyloxycarbonyl (Boc-group). U.S. Pat. No. '737 process involves condensation of Boc-protected Valine with Acyclovir to obtain Boc-protected Valacyclovir, which is subsequently deprotected using hydrochloric acid to obtain Valacyclovir hydrochloride. The process of U.S. Pat. No. '737 is as depicted in scheme 2.

Scheme-2:

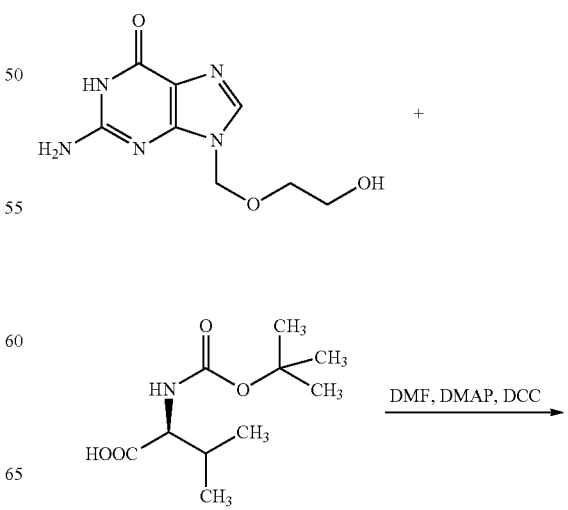

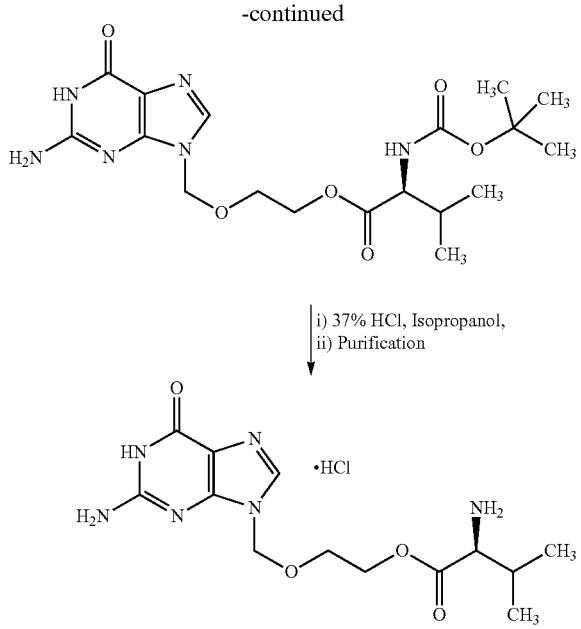

i) 37% HCl, Isopropanol,
ii) Purification

The present inventors have observed that the Valacyclovir product obtained by the process disclosed in U.S. Pat. No. '737 contains higher amount of impurities especially degradation products such as Acyclovir and Guanine. The product obtained by this process requires several purification steps, which results into loss of yield and that makes the process unfeasible for production at large scale.

It has been observed that the problems associated with increased impurities, and the corresponding reduced yields, is due to the higher residence time in the batch mode process disclosed in U.S. Pat. No. '737.

Due to the challenges involved in the processes of the prior art, there is clearly a need for a process for the preparation of valacyclovir that employs less severe deprotecting procedures while retaining the higher purity of the final product.

Hence, present inventors have developed a process for preparing pure Valacyclovir hydrochloride suitable for use in the pharmaceutical composition.

OBJECTIVE OF THE INVENTION

The main objective of the present invention is to provide an improved process for the preparation of Valacyclovir or pharmaceutically acceptable salts thereof.

Another objective of the present invention is to provide a process for the preparation of pure Valacyclovir hydrochloride suitable for use in the pharmaceutical composition.

SUMMARY OF THE INVENTION

In one embodiment, the present invention provides a process for the preparation of Valacyclovir or pharmaceutically acceptable salt thereof, which comprises reaction of amine-protected Valacyclovir or its salt with deprotecting agent in a continuous flow reactor.

In another embodiment, the present invention provides a process for the preparation Valacyclovir hydrochloride, which comprises:
   a) providing a solution of amine-protected Valacyclovir in a suitable solvent to obtain solution A;
   b) providing a solution of deprotecting agent in a suitable solvent to obtain solution B;
   c) feeding separately prepared solution A and solution B to a continuous flow reactor;
   d) continuously eluting the reaction mass from the reactor; and
   e) precipitating the solid from the reaction mass to obtain Valacyclovir hydrochloride.

In another embodiment, the present invention provides a process for the preparation of Valacyclovir hydrochloride, which comprises:
   a) providing a solution of Boc-protected Valacyclovir in a suitable solvent to obtain solution A;
   b) providing aqueous solution of hydrochloric acid to obtain solution B;
   c) feeding separately prepared solution A and solution B to a continuous flow reactor;
   d) continuously eluting the reaction mass from the reactor;
   e) precipitating the solid from the reaction mass; and
   f) drying the product to obtain Valacyclovir hydrochloride.

DETAILED DESCRIPTION OF THE INVENTION

The present invention provides an economical and commercially viable process for producing Valacyclovir or pharmaceutically acceptable salt thereof. The process employs application of reactors such as microreactor, lug flow reactor, microfluidic flow reactor, coil-type flow reactor, tubular flow reactor, laminar flow reactor, packed bed reactor, fluidized bed reactor and fixed bed reactor, for the preparation of Valacyclovir or pharmaceutically acceptable salt thereof in purity greater than 99% with enhanced in-process control on impurities specifically Acyclovir and Guanine.

In one embodiment, the present invention provides a process for the preparation of Valacyclovir or pharmaceutically acceptable salt thereof, which comprises reaction of amine-protected Valacyclovir or its salt with deprotecting agent in a continuous flow reactor.

The reaction of amine-protected Valacyclovir or its salt with deprotecting agent may be performed between solid and solid or solid and solution or between solution of Valacyclovir and solution of deprotecting agent.

Amine-protected Valacyclovir or its salt may be prepared from amine protected valine selected from N-t-butoxycarbonyl valine, N-formyl valine and N-carboxybenzyl valine, and acyclovir. Salt of Amine-protected Valacyclovir may be selected from hydrochloride, hydrobromide, acetate, oxalate, succinate, sulfate, phosphate and the like.

Valacycovir or pharmaceutically acceptable salt thereof and deprotecting agent can be added into the reactor at a temperature of about 0 to 100° C.

When the reaction between solutions, the solution of Valacyclovir or deprotecting agent is provided by dissolution of solid in a solvent or the solution can be taken from the previous reaction step. The solvent is used for dissolution is selected from same or different solvent of water, alcohols, hydrocarbons and chlorinated solvents or mixture thereof. The solution can be prepared at a temperature of about 0 to 50° C. or at reflux of solvent used.

The solution is flowed with same or different rate continuously into the reactor. The flow rate may be 1 ml/minute to 50 ml/minute at a temperature of about 0 to 100° C. or above. In an embodiment, the flow rate of Valacyclovir may be more than the flow rate of the solution of deprotecting agent.

After the reaction, the obtained reaction elute may be subjected for solid isolation using suitable techniques such as acid/base treatment, recrystallization, anti-solvent, crash cooling, spray drying and the like.

The resultant Valacyclovir or pharmaceutically acceptable salt has the purity of greater than 98% or greater than 99% or greater than 99.5% determined by HPLC.

In another embodiment, the present invention provides a process for the preparation Valacyclovir hydrochloride, which comprises:
 a) providing a solution of amine-protected Valacyclovir in a suitable solvent to obtain solution A;
 b) providing a solution of deprotecting agent in suitable solvent to obtain solution B;
 c) feeding separately prepared solution A and solution B to a continuous flow reactor;
 d) continuously eluting the reaction mass from the reactor; and
 e) precipitating the solid from the reaction mass to obtain Valacyclovir hydrochloride Amine-protected Valacyclovir is protected with a suitable protecting group, which can be deprotected by using less severe deprotection methods such by using suitable acid. One of the suitable protecting group according to present invention is tert-butoxycarbonyl group (Boc). The amine protected Valacyclovir may be prepared by condensation of Acyclovir with corresponding amine-protected Valine or salt thereof in presence of suitable coupling agents selected from the group comprising of dicyclohexylcarbodiimide (DCC) or N,N'-diisopropylcarbodiimide (DIC).

The solvent used for the preparation of solution of A and solution of B may be selected from same or different solvent. The solvent used for the preparation of solution A is selected from the group comprising of lower alcohols such as methanol, ethanol, propanol, isopropanol, butanol and isoamyl alcohol; hydrocarbons such as toluene, heptane, hexane, cyclohexane; chlorinated solvent such as methylene chloride, chloroform and carbon tetrachloride; or mixtures thereof.

The Solution-B is prepared by adding suitable deprotecting agent is acid to a suitable solvent. The acid is selected from the group comprising of hydrochloric acid, trifluoroacetic acid, phosphoric acid, formic acid or mixture thereof. The solvent is selected from the group comprising of water, lower alcohols such as methanol, ethanol, isopropanol or mixtures thereof.

The Solution A and Solution B are fed simultaneously into the continuous mode reactor in a continuous flow. The solution A is added to the reactor at a flow rate of 5-15 ml/minute and preferably at about 8-10 ml/min. The solution B is added to the reactor at a rate of 2-10 ml/min and preferably at about 4-8 ml/min. The reaction mass is passed through a continuous mode reactor at a residence time of 1-15 minute and preferably at 2-5 minute. The reaction mass is passed at temperature 10-120° C. and preferably at 80-100° C. The reaction mass eluted from the reactor is continuously collected for the isolation of product.

The aqueous layer containing Valacyclovir product from the eluted reaction mass may be separated by conventional methods. The excess of deprotecting agent used for deprotection may be quenched by adding suitable base selected from the organic base selected from the group comprising of triethylamine, diisopropylamine, diisopropylethylamine, or inorganic base selected from sodium bicarbonate, ammonia, potassium bicarbonate and sodium carbonate. The resultant aqueous solution may be subjected for precipitation by using conventional methods.

The solid is isolated using suitable techniques such as filtration, decantation, centrifugation and the like. The solid obtained from the present invention is further dried at a temperature of about 20 to about 100° C. under vacuum.

When the resultant compound from the reaction is Valacyclovir or its salt of other than hydrochloride, the resultant compound is converted into Valacyclovir hydrochloride salt by treating with hydrochloric acid.

In another embodiment, the present invention provides a process for the preparation of Valacyclovir hydrochloride, which comprises:
 a) providing a solution of Boc-protected Valacyclovir in a suitable solvent to obtain solution A;
 b) providing aqueous solution of hydrochloric acid to obtain solution B;
 c) feeding separately prepared solution A and solution B to a continuous flow reactor;
 d) continuously eluting the reaction mass from the reactor;
 e) precipitating the solid from the reaction mass; and
 f) drying the product to obtain Valacyclovir hydrochloride The step a) involves providing a solution of Boc-protected Valacyclovir in a suitable solvent to obtain solution A.

The solution can be prepared by dissolution of Boc-protected Valacyclovir in a solvent or the solution can be taken from the previous reaction step. The dissolution may be performed by combining Boc-protected Valacyclovir in a solvent at a temperature of about 0 to about 100° C. or at a reflux temperature of solvent used. The solvent used for preparation of solution may be pre-heated or pre-cooled. The quantity of solvent used for providing solution may be in the range of about 2-20 ml per gram of Boc-protected Valacyclovir.

The solvent used for providing solution is selected from water, methanol, ethanol, propanol, isopropanol, butanol, isoamyl alcohol, toluene, heptane, hexane, cyclohexane, methylene chloride, chloroform, ethyl acetate, methyl acetate, isopropyl acetate, acetone, dimethyl formamide, dimethyl acetamide and tetrahydrofuran; or mixtures thereof.

The step b) involves providing aqueous solution of hydrochloric acid to obtain solution B.

The solution of deprotecting agent such as hydrochloric acid is prepared by combining conc. hydrochloric acid with water or alcohol such as methanol, ethanol, isopropyl alcohol and the like or mixtures thereof at a temperature of about 0° C. to 50° C. The solution of step b) may be prepared in water and then combined with alcohol.

The step c) involves feeding separately prepared solution A and solution B to a continuous flow reactor.

The Solution A and Solution B are fed simultaneously into the continuous mode reactor in a continuous flow. The solution A is added to the reactor at a flow rate of about 8-10 ml/min. The solution B is added to the reactor at a rate of about 4-8 ml/min. The reaction mass is passed through a continuous mode reactor at a residence time of 2-5 minute.

The step d) involves continuously eluting the reaction mass from the reactor.

The reaction mass is eluted from the reactor continuously. The reaction mass is collected from reactor and is subjected for layer separation. The pH of aqueous layer may be adjusted to 2 to 4 with base such as triethylamine, diisopropylamine, diisopropylethylamine.

The step e) involves precipitating the solid from the reaction mass.

The aqueous layer obtained from step d) is subjected for solid precipitation using anti-solvent technique, distillation, recrystallization or combination thereof. The solvent used for solid precipitation is selected from alcohol such as ethanol.

The solution of step d) may be combined with alcohol at a lower temperature of about 25° C. or below and then concentrated or stirred for a period of about 30 minutes or above to afford complete precipitation.

The step f) involves drying the product to obtain Valacyclovir hydrochloride.

The resultant solid is dried at about 30° C. or above for a period of about 1 to 10 hours or more without effecting quality of the product.

Drying may be suitably carried out in equipment such as a tray dryer, vacuum oven, air oven, or using a fluidized bed drier, spin flash dryer, flash dryer, and the like.

The drying may be carried out at reduced pressures, such as below about 650 mm Hg, or below about 50 mm Hg.

In another embodiment, a process for preparation of Valacyclovir hydrochloride having particle size of D(0.9) less than 500μ, which comprises providing solution of Valacyclovir hydrochloride in water or water and water miscible organic solvent, adding ketone solvent in lot wise and recovering the solid of Valacyclovir hydrochloride.

The solution may be provided by the dissolution of Valacyclovir in water or water and water miscible solvent such as alcohol, for example, methanol at a temperature of about 20° C. or above. The temperature used for dissolution is about 30 to about 50° C.

To the solution of Valacyclovir hydrochloride, ketone such as acetone is added in lot wise and optionally, the solution is seeded with Valacyclovir hydrochloride. The solid is recovered by filtration or decantation to afford Valacyclovir hydrochloride having particle size of D(0.9) less than 500μ or less than 400μ and D(0.5) less than 200μ or less than 150μ.

In yet another embodiment of the present invention, Valacyclovir hydrochloride prepared according to present invention is converted to its pharmaceutical composition.

The invention is illustrated with the following examples, which are provided by way of illustration only and should not be construed to limit the scope of the invention.

Example 1

Process for the Preparation of Boc-L-Valacyclovir

BOC L-Valine (120 g) was dissolved in 300 ml dimethylformamide (DMF) at 25-30° C. The solution was cooled to −5° C. and DCC solution (137.47 g DCC in 350 ml DMF) was added at −5 to −10° C. in 90 min followed by stirring for 10 min at −5 to 10° C. Acyclovir (100 g) was added to the obtained solution of Boc-Valine, followed by 4-dimethylaminopyridine (DMAP) (7 g) was added at −5 to −10° C. After completion of the reaction, residue was washed with DMF (100 ml) and DMF was distilled out under vacuum at 55-60° C. Preheated DM water (2 lit) was added to the above residue at 70-75° C. and stirred for 60 min at 70-75° C. and cooled to 30-35° C. The product was filtered and washed with 300 ml DM water at 35-45° C.; and further washed with 150 ml ethanol and dried the product at 45-50° C.

Yield: Dry—205 g crude
Purity: 97.5 to 98% (by HPLC)

Example 2

Process for the Preparation of Valacyclovir Hydrochloride
Preparation of Solution-A Boc-L-Valacyclovir crude (50 g) was charged into mixture of methylene chloride (375 ml) and methanol (125 ml) at 25-30° C. and stirred the reaction mass at 25-30° C. to get the clear solution-A.

Preparation of Solution-B

Conc. Hydrochloric acid (56 ml) was added to DM water (224 ml) over a period of 15-20 min at 20-25° C. Thereafter methanol (56 ml) was added slowly to the obtained solution at 20-25° C.

Above separately prepared solution-A (Flow rate-8 ml/min) and solution-B (Flow rate-5.5 ml/min) were fed to the continuous flow micro reactor at 80° C. The elute reaction mass from micro reactor was continuously collected at 0-5° C. As the feed solutions A & B are consumed micro reactor is flush with methylene chloride (50 ml: 50 ml) each feed. Immediately after the collection of reaction mass, aqueous layer and lower organic layers were separated. The pH of the aqueous layer containing product was adjusted to about 2.5 to 2.8 with triethyl amine (~46.28 g) at 0-5° C.). Ethanol (300 ml) at 0-5° C. was added slowly to the solution. The obtained reaction mass was distilled under reduced pressure (400-40 mm Hg) to get white. The obtained solid mass was cooled at 25-30° C. and ethanol (300 ml) was added and continued stiffing the above slurry mass at 25-30° C. for 60-80 min. The solid was filtered and washed with chill ethanol (100 ml. 0-5° C.). The obtained solid is dried in vacuum dryer at 40-45° C. till moisture content is 5-8%.

Yield: 31 g
Purity: 99% (by HPLC)

Comparative Example

Process for the Preparation of Valacyclovir Hydrochloride

Boc-L-Valacyclovir (50 g) was charged into DM Water (50 ml) at 20-25° C. to obtain a suspension. Then concentrated hydrochloric acid (23.29 g) was added slowly to the obtained solution over a period of 15-20 min at 20-25° C. and stirred for about 2.5 hours. After completion of the reaction, iso-propanol (1100 ml) was added over a period of 2 hours and stirred the mixture to 0-5° C. for 1 hour. The obtained solid was filtered under nitrogen atmosphere and washed with isopropanol (150 ml). The obtained solid was dried under vacuum at 40-45° C. till moisture is in the range of 5% to 8%.

Yield: 11.8 g
Purity: 96.64% (by HPLC),
Impurities: Acyclovir 2.45%, Guanine 0.24%.

We claim:
1. A process for the preparation of Valacyclovir hydrochloride, which comprises:
   a) providing a solution of Boc-protected Valacyclovir in a suitable solvent, selected from methanol and methylene chloride or mixture thereof, to obtain solution A;
   b) providing aqueous solution of hydrochloric acid to obtain solution B;
   c) feeding separately prepared solution A and solution B to a continuous flow reactor at a temperature of about 80-100 C;
   d) continuously eluting the reaction mass from the reactor;
   e) precipitating the solid from the reaction mass; and f) drying the product to obtain Valacyclovir hydrochloride.

2. A process for the preparation of Valacyclovir hydrochloride, which comprises:
   a) providing a solution of Boc-protected Valacyclovir in a suitable solvent, selected from an alcohol and chlorinated solvent or mixture thereof, to obtain solution A;
   b) providing aqueous solution of hydrochloric acid and adding methanol to obtain solution B;
   c) feeding separately prepared solution A and solution B to a continuous flow reactor at a temperature of about 80-100 C;
   d) continuously eluting the reaction mass from the reactor;
   e) precipitating the solid from the reaction mass; and
   f) drying the product to obtain Valacyclovir hydrochloride.

\* \* \* \* \*